United States Patent [19]

Yamada et al.

[11] Patent Number: 5,447,847

[45] Date of Patent: Sep. 5, 1995

[54] QUANTITATIVE DETERMINATION OF PYRUVIC ACID AND QUANTITATIVE ANALYSIS FOR COMPONENT OF LIVING BODY MAKING USE OF SUCH DETERMINATION

[75] Inventors: Yayoi Yamada, Souwa; Kazuaki Yoshikawa, Tokyo, both of Japan

[73] Assignee: Nissui Pharmaceutical Co., Ltd., Tokyo, Japan

[21] Appl. No.: 114,844

[22] Filed: Sep. 2, 1993

[51] Int. Cl.$^6$ .......................... C12Q 1/00; C12Q 1/32
[52] U.S. Cl. ............................ 435/26; 435/4; 435/7.4; 435/7.91; 435/25
[58] Field of Search ............... 435/25, 26, 4, 7.91, 435/7.4

[56] References Cited

U.S. PATENT DOCUMENTS 4,923,796  5/1990  Deneke .................. 435/15

FOREIGN PATENT DOCUMENTS 5-95798  4/1993  Japan .

OTHER PUBLICATIONS

Sigma Catalog, 1993, (published 1992), p. 866.
Methods in Enzymology, vol. 89, (1982), pp. 35–40.
Biochemical Medicine, vol. 29, pp. 51–56 (1983).
Rupert et al., Tetrahedron Letters, vol. 28, No. 52, pp. 6583–6586 (1987).
Singleton et al., Dictionary of Microbiology and Molecular Biology, (1987), (p. 978).

*Primary Examiner*—Michael G. Wityshyn
*Assistant Examiner*—Jane Williams
*Attorney, Agent, or Firm*—Oblon, Spivak, McClelland, Maier & Neustadt

[57]  ABSTRACT

Disclosed herein is a quantitative determination of pyruvic acid, which comprises reacting oxidized nicotinamide adenine dinucleotide, a pyruvate dehydrogenase complex and coenzyme A to a specimen and measuring the amount of the resulting reduced nicotinamide adenine dinucleotide. A quantitative analysis for a component of a living body, in which the quantitative determination is used, is also disclosed. Pyruvic acid or other components existing in a living body or formed in the course of a reaction in the living body can be quantitatively determined simply and precisely.

17 Claims, 4 Drawing Sheets

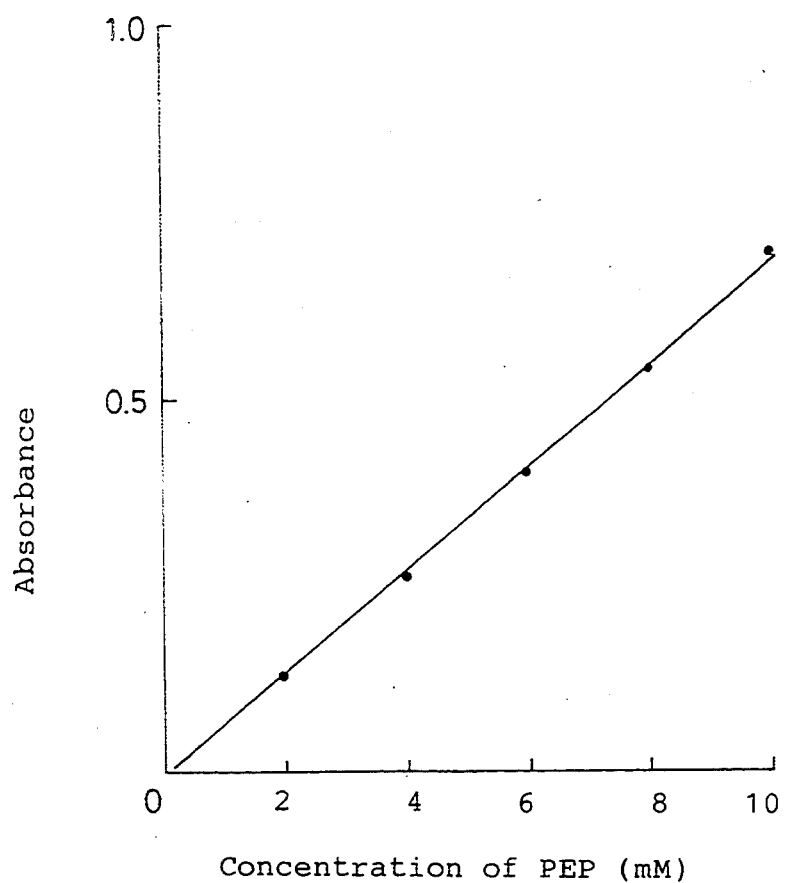

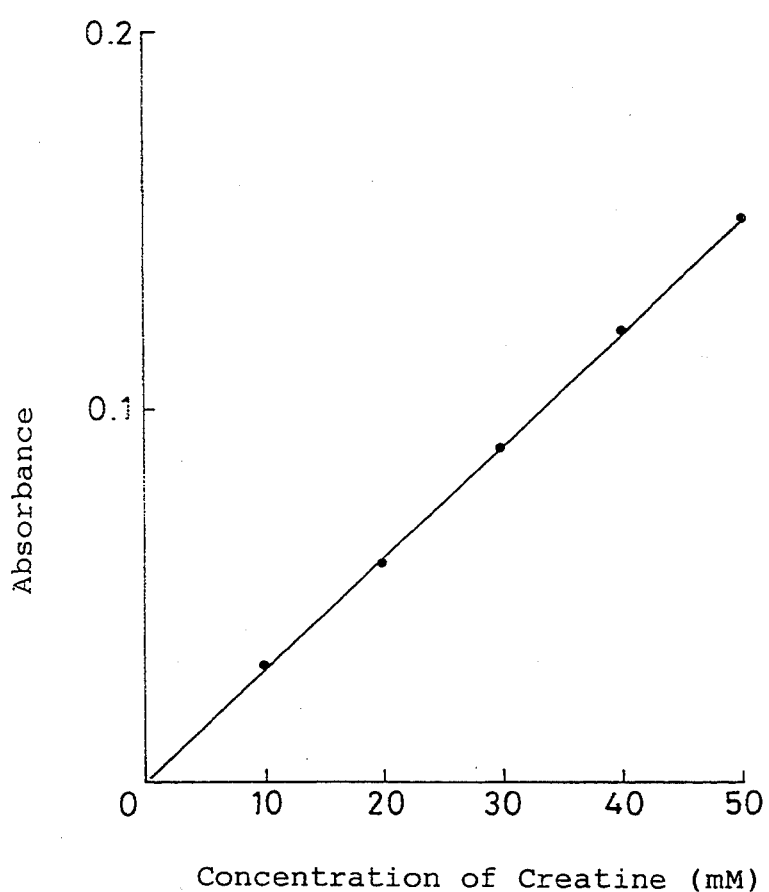

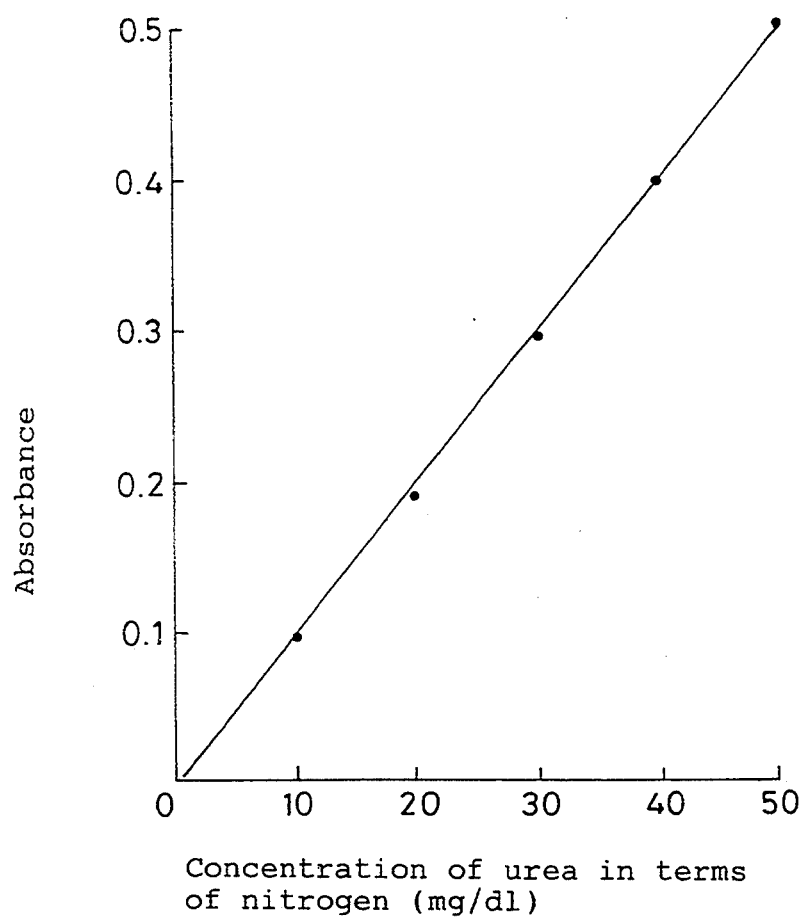

QUANTITATIVE DETERMINATION OF PYRUVIC ACID AND QUANTITATIVE ANALYSIS FOR COMPONENT OF LIVING BODY MAKING USE OF SUCH DETERMINATION

BACKGROUND OF THE INVENTION i) Field of the Invention

The present invention relates to a quantitative determination of pyruvic acid and a quantitative analysis for a component of a living body making use of such a determination.

ii) Description of the Background Art

In the field of clinical chemistry, there are generally used processes for the quantitative analysis for a component of a living body in which the component of the living body is oxidized in the presence of an oxidase to form hydrogen peroxide, and the resulting hydrogen peroxide is converted into a quinone type pigment with a peroxidase and a color former, thereby conducting colorimetry, and in which an oxidation-reduction reaction between oxidized nicotinamide adenine dinucleotide (hereinafter referred to as "NAD") and reduced nicotinamide adenine dinucleotide (hereinafter referred to as "NADH") by a dehydrogenase is used to determine increase or decrease in the absorbance of NADH at a wavelength of 340 nm.

When the amount of pyruvic acid existing in a living body or formed in the course of a biological reaction is determined, it is known to oxidize pyruvic acid with a pyruvate oxidase to form hydrogen peroxide and then convert hydrogen peroxide thus formed into a quinone type pigment with a peroxidase and a color former, thereby conducting colorimetry. It is also known to react a lactate dehydrogenase and NADH with pyruvic acid existing in a living body or formed in the course of a biological reaction and determine decrease in the absorbance of NADH at a wavelength of 340 nm.

The process in which hydrogen peroxide formed by the pyruvate oxidase is determined however involves problems such that a negative error is produced by reducing substances among the components of the living body, for example, ascorbic acid, bilirubin and the like, and when the concentration of pyruvic acid is high, dissolved oxygen in a reaction reagent becomes insufficient, resulting in a failure in determination.

On the other hand, the process in which the lactate dehydrogenase is used to determine decrease in the absorbance of NADH at a wavelength of 340 nm can widen the measuring range in dependence on the concentration of NADH, but involves a problem that when the concentration of NADH is increased, an initial absorbance is also increased, so that the measurement of the absorbance becomes impossible from the viewpoint of the performance of a spectrophotometer.

SUMMARY OF THE INVENTION

In view of the foregoing circumstances, the present inventors have carried out an extensive investigation as to the quantitative determination of pyruvic acid existing in a living body or formed in the course of a biological reaction. As a result, it has been found that when NAD, a pyruvate dehydrogenase complex and coenzyme A (hereinafter referred to as "CoA") are reacted to a specimen to measure the amount of the resulting NADH, the above-mentioned problems can be solved, leading to completion of the present invention.

In an aspect of the present invention, there is thus provided a quantitative determination of pyruvic acid, which comprises reacting NAD, a pyruvate dehydrogenase complex and CoA to a specimen and measuring the amount of the resulting NADH.

In another aspect of the present invention, there is also provided a quantitative analysis for a component of a living body, said component being to be converted into pyruvic acid as a result of its reaction, which comprises reacting a reagent capable of converting the component in a specimen into pyruvic acid, NAD, a pyruvate dehydrogenase complex and CoA to the specimen and measuring the amount of the resulting NADH.

According to the present invention, the amount of pyruvic acid existing in a living body or formed in the course of a reaction in the living body can be determined simply, speedily and precisely. In addition, the use of the above quantitative determination makes it possible to quantitatively analyze for other components of the living body.

BRIEF DESCRIPTION OF THE DRAWINGS

FIG. 2 is a graph illustrating a calibration curve as to phosphoenolpyruvic acid (hereinafter referred to as "PEP"), obtained in Example 2;

FIG. 3 is a graph illustrating a calibration curve as to creatine, obtained in Example 3; and FIG. 4 is a graph illustrating a calibration curve as to urea, obtained in Example 4.

DETAILED DESCRIPTION OF THE INVENTION AND PREFERRED EMBODIMENTS

Figure 1:
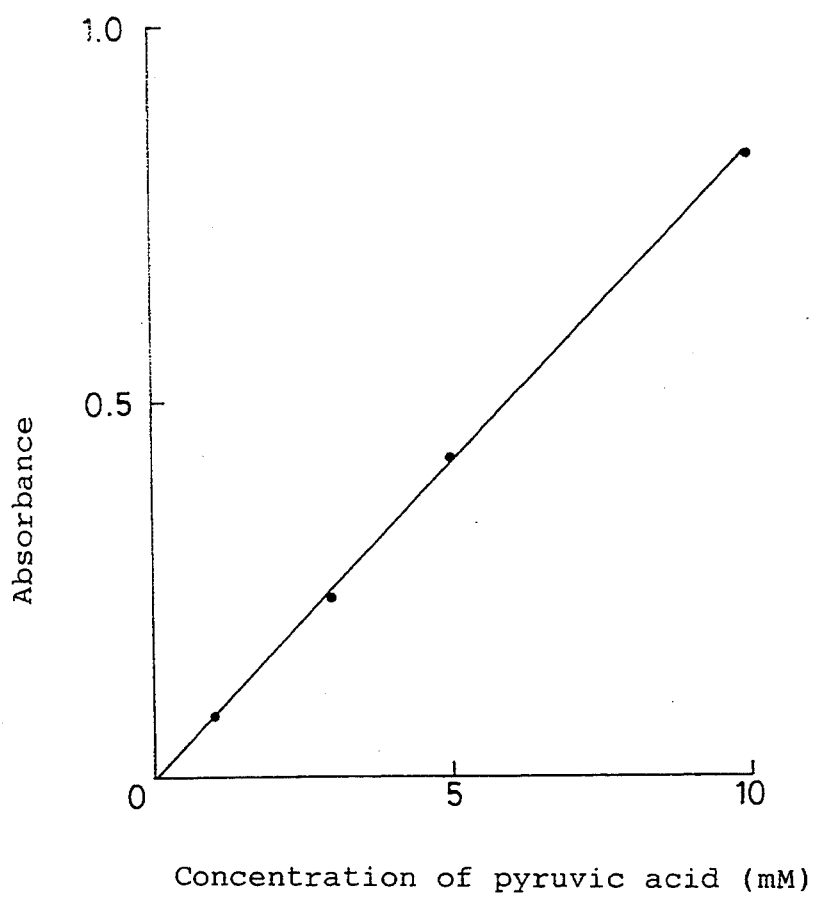
FIG. 1 is a graph illustrating a calibration curve as to pyruvic acid, obtained in Example 1.

The quantitative determination of pyruvic acid according to the present invention is represented by the following reaction scheme:

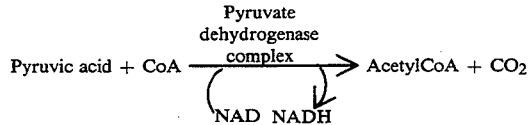

In the above reaction, NADH is formed in dependence on the concentration of pyruvic acid. In NADH, absorption appears at a wavelength of 340 nm. Therefore, the measurement of absorbance at such a wavelength makes it possible to determine the amount of the intended pyruvic acid.

Specimens in the present invention include live humors such as blood, plasma and urine, pyruvic acid solutions, etc.

To perform the quantitative determination according to the present invention, for example, it is only necessary to add a buffer solution containing 0.1–10 mM of NAD, 0.05–20 U/ml of a pyruvate dehydrogenase complex and 0.1–5 mM of CoA to a specimen, react them for 2–30 minutes near at 37° C., and measure an absorbance at a wavelength of 340 nm. The above buffer solution may be added with 0.01–20 mM of calcium ions, 0.01–20 mM of magnesium ions and/or 0.1–10 mM of thiamine pyrophosphate for the purpose of activating and stabilizing the pyruvate dehydrogenase complex. Calcium chloride, calcium acetate or the like may be used as a source for the calcium ions, while magnesium chloride, magnesium sulfate, magnesium acetate or the like may be used as a source for the magnesium ions.

Pyruvic acid is important as an intermediate in a metabolic pathway in a living body, and in the living body, there are many metabolic pathways for forming pyruvic acid. Therefore, when the determination of a component of the living body, which is to be converted into pyruvic acid as a result of its reaction, is attempted, the intended component of the living body can be quantitatively analyzed by combining a known reagent capable of converting the component in a specimen into pyruvic acid with the above-described reaction.

For example, the combination of a pyruvate kinase with adenosine diphosphate (hereinafter referred to as "ADP") makes it possible to determine PEP.

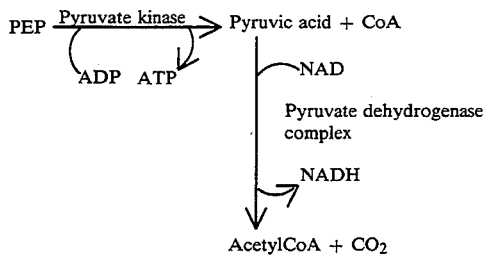

Besides, creatine can also be determined by using a creatine kinase prior to the above reaction. The process of the reaction is represented below.

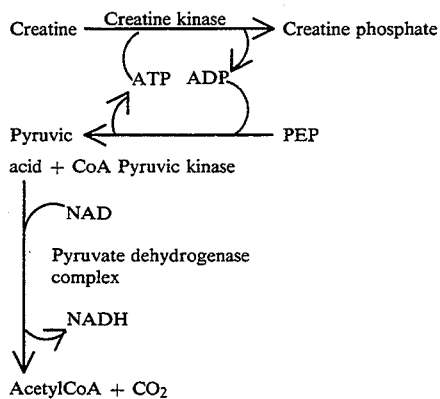

Further, urea can be determined by using a urea amide lyase in place of the creatine kinase. The process of the reaction is represented below.

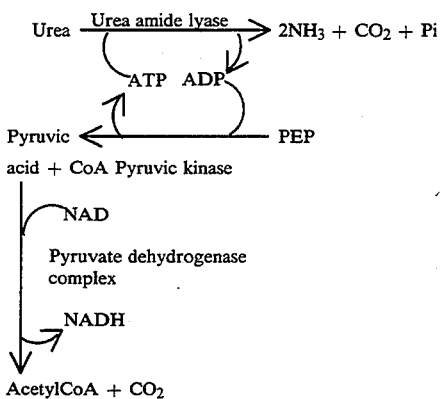

As described above, the amount of pyruvic acid existing in a living body or formed in the course of a reaction in the living body can be determined by measuring the absorbance at 340 nm of NADH formed at the same time. Further, PEP, urea, creatine, creatinine, glucose, neutral fats and the like, which are components of a living body, can be quantitatively determined according to the above quantitative determination.

The present invention will hereinafter be described specifically by the following examples. However, it should be borne in mind that the present invention is not limited to and by these examples only.

EXAMPLE 1

Quantitative determination of pyruvic acid:

| Reaction reagent: | |
| --- | --- |
| Phosphate buffer (pH: 6.5) | 50 mM |
| Thiamine pyrophosphate | 0.2 mM |
| NAD | 1 mM |
| Calcium chloride | 1 mM |
| CoA | 0.2 mM |
| Pyruvate dehydrogenase complex | 0.5 U/ml |

To each 5 μl of aqueous solutions of 1 to 10 mM of pyruvic acid, were added 300 μl of the above reagent to react them for 10 minutes at 37° C. Thereafter, the absorbances of the resulting reaction mixtures at a wavelength of 340 nm were measured. A graph obtained as the result of the measurement and showing the relationship between the concentration of pyruvic acid and the absorbance is illustrated in FIG. 1.

EXAMPLE 2

Quantitative determination of PEP:

| Reaction reagent 1: | |
| --- | --- |
| N,N-Bis(2-hydroxyethyl)-2-aminoethane sulfonic acid (hereinafter called "BES", pH: 7.1) buffer | 50 mM |
| Thiamine pyrophosphate | 0.2 mM |
| NAD | 1 mM |
| Calcium chloride | 1 mM |
| CoA | 0.2 mM |
| Pyruvate dehydrogenase complex | 0.5 U/ml |
| Reaction reagent 2: | |
| BES buffer (pH: 7.1) | 50 mM |
| ADP | 3 mM |
| Magnesium chloride | 16 mM |
| Pyruvate kinase | 6 U/ml |

To each 5 μl of aqueous solutions of 2 to 10 mM of PEP, were added 300 μl of the reaction reagent 1 and 100 μl of the reaction reagent 2 to react them for 5 minutes at 37° C. Thereafter, the absorbances of the resulting reaction mixtures at a wavelength of 340 nm were measured. A graph obtained as the result of the measurement and showing the relationship between the concentration of PEP and the absorbance is illustrated in FIG. 2.

EXAMPLE 3

Quantitative determination of creatine:

| Reaction reagent 1: | |
| --- | --- |
| BES buffer (pH: 7.4) | 50 mM |
| Thiamine pyrophosphate | 0.3 mM |
| NAD | 1.5 mM |

| -continued | |
|---|---|
| Magnesium acetate | 10 mM |
| CoA | 1.5 mM |
| Pyruvate dehydrogenase complex | 0.75 U/ml |
| Reaction reagent 2: | |
| BES buffer (pH: 7.1) | 50 mM |
| ATP | 4.5 mM |
| PEP | 4.5 mM |
| Magnesium acetate | 10 mM |
| Pyruvate kinase | 3 U/ml |
| Creatine kinase | 20 U/ml |

To each 5 μl of aqueous solutions of 10 to 15 mM of creatine, were added 200 μl of the reaction reagent 1 and 200 μl of the reaction reagent 2 to react them for 5 minutes at 37° C. Thereafter, the absorbances of the resulting reaction mixtures at a wavelength of 340 nm were measured. A graph obtained as the result of the measurement and showing the relationship between the concentration of creatine and the absorbance is illustrated in FIG. 3.

EXAMPLE 4

Quantitative determination of creatine:

| Reaction reagent 1: | |
|---|---|
| BES buffer (pH: 7.1) | 50 mM |
| Thiamine pyrophosphate | 2.7 mM |
| NAD | 1.5 mM |
| Magnesium chloride | 10 mM |
| CoA | 1.5 mM |
| PEP | 2 mM |
| ATP | 2 mM |
| Pyruvate kinase | 6 U/ml |
| Pyruvate dehydrogenase complex | 0.75 U/ml |
| Reaction reagent 2: | |
| BES buffer (pH: 7.1) | 50 mM |
| Potassium hydrogencarbonate | 20 mM |
| Urea amide lyase | 0.4 U/ml |

To each 2 μl of aqueous solutions of 10 to 50 mg/dl, in terms of nitrogen, of urea, were added 200 μl of the reaction reagent 1 and 200 μl of the reaction reagent 2 to react them for 5 minutes at 37° C. Thereafter, the absorbances of the resulting reaction mixtures at a wavelength of 340 nm were measured. A graph obtained as the result of the measurement and showing the relationship between the concentration of urea in terms of nitrogen and the absorbance is illustrated in FIG. 4.

It has become clear that there is a linear relationship between the amounts of the components determined and the absorbances at the wavelength of 340 nm in Examples 1-4. It is therefore possible to quantitatively determine a component in an unknown concentration in a specimen using any one of such graphs as a calibration curve.

What is claimed is:

1. A method of quantitatively determining the amount of pyruvic acid in a sample, comprising the steps of:
    contacting NAD, pyruvate dehydrogenase complex and coenzyme A with a sample containing pyruvic acid to produce NADH in an amount which corresponds to the amount of pyruvic acid in said sample, and
    measuring the amount of NADH which is produced.

2. The method of claim 1, wherein said sample is selected from the group consisting of blood, plasma and urine.

3. The method of claim 1, wherein said contacting step comprises contacting the sample with a buffer solution containing 0.1-10 mM of NAD, 0.05-20 U/ml of pyruvate dehydrogenase complex and 0.1-5 mM of coenzyme A.

4. The method of claim 3, wherein said buffer solution further contains at least one substance selected from the group consisting of calcium ions and magnesium ions.

5. The method of claim 3, wherein said buffer solution further contains thiamine pyrophosphate.

6. The method of claim 1, wherein said measuring step comprises measuring the absorbance of the contacted sample at a wavelength of 340 nm.

7. A method of quantitatively determining the amount of a metabolite which is enzymatically converted into pyruvic acid by the action of an enzyme, comprising the steps of:
    contacting a sample containing said metabolite with NAD, pyruvate dehydrogenase complex, coenzyme A and said enzyme to form NADH, in an amount which corresponds to the amount of the metabolite present in the sample, and
    measuring the amount of NADH produced.

8. The method of claim 7, wherein said metabolite is selected from the group consisting of phosphoenolpyruvic acid, urea, creatinine, creatine, glucose and a neutral fat.

9. The method of claim 8, wherein said metabolite is phosphoenolpyruvic acid and said enzyme is pyruvate kinase.

10. The method of claim 8, wherein said metabolite is creatine and said enzyme is a mixture of pyruvate kinase and creatine kinase.

11. The method of claim 8, wherein said metabolite is urea and said enzyme is a mixture of pyruvate kinase and urea amide lyase.

12. The method of claim 7, wherein said sample is selected from the group consisting of blood, plasma and urine.

13. The method of claim 7, wherein said contacting step comprises contacting the sample with a buffer solution containing 0.1-10 mM of NAD, 0.05-20 U/ml of pyruvate dehydrogenase complex and 0.1-5 mM of coenzyme A.

14. The method of claim 13, wherein said buffer solution further contains a member selected from the group consisting of calcium ions and magnesium ions.

15. The method of claim 13, wherein said buffer solution further contains thiamine pyrophosphate.

16. The method of claim 7, wherein said measuring step comprises measuring the absorbance of said contacted sample at a wavelength of 340 nm.

17. The method of claim 7, wherein there is a 1:1 correspondence between the amount of NADH formed and the amount of metabolite in the sample.

* * * * *